US009586981B2

(12) United States Patent
Rosebrugh et al.

(10) Patent No.: US 9,586,981 B2
(45) Date of Patent: Mar. 7, 2017

(54) Z-SELECTIVE METATHESIS CATALYSTS

(71) Applicant: CALIFORNIA INSTITUTE OF TECHNOLOGY, Pasadena, CA (US)

(72) Inventors: Lauren E. Rosebrugh, Pasadena, CA (US); Myles B. Herbert, Somerville, MA (US); Vanessa M. Marx, Los Angeles, CA (US); Benjamin K. Keitz, San Francisco, CA (US); Robert H. Grubbs, South Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 14/649,725

(22) PCT Filed: Dec. 12, 2013

(86) PCT No.: PCT/US2013/074783
§ 371 (c)(1),
(2) Date: Jun. 4, 2015

(87) PCT Pub. No.: WO2014/093687
PCT Pub. Date: Jun. 19, 2014

(65) Prior Publication Data
US 2015/0299236 A1    Oct. 22, 2015

Related U.S. Application Data

(60) Provisional application No. 61/736,443, filed on Dec. 12, 2012.

(51) Int. Cl.
| | |
|---|---|
| *C07F 15/00* | (2006.01) |
| *B01J 31/22* | (2006.01) |
| *C08G 61/08* | (2006.01) |
| *C07C 2/34* | (2006.01) |
| *C07C 29/00* | (2006.01) |
| *C07C 45/67* | (2006.01) |
| *C07C 67/293* | (2006.01) |
| *C07D 313/00* | (2006.01) |
| *C08F 110/14* | (2006.01) |

(52) U.S. Cl.
CPC ....... *C07F 15/0046* (2013.01); *B01J 31/2265* (2013.01); *B01J 31/2278* (2013.01); *C07C 2/34* (2013.01); *C07C 29/00* (2013.01); *C07C 45/673* (2013.01); *C07C 67/293* (2013.01); *C07D 313/00* (2013.01); *C08F 110/14* (2013.01); *C08G 61/08* (2013.01); *B01J 2231/20* (2013.01); *B01J 2231/32* (2013.01); *B01J 2531/821* (2013.01); *C08G 2261/418* (2013.01)

(58) Field of Classification Search
CPC . B01J 23/462; C07C 2/00; C07C 6/04; C07C 13/00; C07C 2523/46; C07C 45/61; C07C 45/673; C07F 15/0046
See application file for complete search history.

(56) References Cited

U.S. PATENT DOCUMENTS

| | | | |
|---|---|---|---|
| 5,312,940 A | 5/1994 | Grubbs et al. | |
| 6,620,955 B1 | 9/2003 | Pederson et al. | |
| 6,921,735 B2 | 7/2005 | Hoveyda et al. | |
| 7,026,495 B1 | 4/2006 | Pederson et al. | |
| 8,987,531 B2 * | 3/2015 | Grubbs | C07C 29/32 560/261 |
| 9,073,801 B2 * | 7/2015 | Hoveyda | C07D 313/00 540/451 |
| 2003/0236427 A1 | 12/2003 | Grubbs et al. | |
| 2005/0131233 A1 | 6/2005 | Fogg et al. | |
| 2006/0128912 A1 | 6/2006 | Piers et al. | |
| 2007/0032667 A1 | 2/2007 | Bonrath et al. | |
| 2007/0043180 A1 | 2/2007 | Zhan | |
| 2010/0144987 A1 | 6/2010 | Vougioukaiakis et al. | |
| 2011/0124868 A1 * | 5/2011 | Grubbs | C07C 67/333 546/4 |
| 2013/0231499 A1 | 9/2013 | Grubbs et al. | |
| 2014/0106960 A1 | 4/2014 | Endo et al. | |

FOREIGN PATENT DOCUMENTS

| | | |
|---|---|---|
| CN | 101594937 A | 12/2009 |
| EP | 2255877 A1 | 12/2010 |
| WO | 02/14376 A2 | 2/2002 |
| WO | WO 2012/097379 A2 * | 7/2012 ............ B01J 23/46 |

OTHER PUBLICATIONS

Keitz, B.K.; Endo, K.; Patel, P.R.; Herbert, M.B.; Grubbs, R.H. J. Am. Chem. Soc. 2011, 134, 693-699.*
Keitz, B.K.; Fedorov, A.; Grubbs, R.H. J. Am. Chem. Soc. 2012, 134, 2040-2043.*
Keitz, B.K.; Endo, K.; Herbert, M.B.; Grubbs, R.H. J. Am. Chem. Soc. 2011, 133, 9686-9688.*
International Search Report and Written Opinion for PCT/US13/74783 dated Apr. 21, 2014.
International Preliminary Report on Patentability for PCT/US13/74783 dated Jun. 25, 2015.
Keitz et al., "Improved Ruthenium Catalysts for Z-Selective Olefin Metathesis," J. Am. Chem. Soc. 134(1):693-699 (2012).
Burling et al., "Coordination, Agostic Stabilization, and C-H Bond Activation of N-Alkyl Heterocyclic Carbenes by Coordinatively Unsaturated Ruthenium Hydride Chloride Complexes," Organometallics, 2009, 28, pp. 6676-6686.

(Continued)

*Primary Examiner* — Rip A Lee
(74) *Attorney, Agent, or Firm* — J.A. Lindeman & Co., PLLC

(57) ABSTRACT

A novel chelated ruthenium-based metathesis catalyst bearing an N-2,6-diisopropylphenyl group is reported and displays near-perfect selectivity for the Z-olefin (>95%), as well as unparalleled TONs of up to 7,400, in a variety of homodimerization and industrially relevant metathesis reactions. This derivative and other new catalytically-active species were synthesized using an improved method employing sodium carboxylates to induce the salt metathesis and C—H activation of these chelated complexes. All of these new ruthenium-based catalysts are highly Z-selective in the homodimerization of terminal olefins.

3 Claims, No Drawings

(56) References Cited

OTHER PUBLICATIONS

Chatterjee et al., "A General Model for Selectivity in Olefin Cross Metathesis," J. Am. Chem. Soc., 2003, 125, pp. 11360-11370.
Endo et al., "Chelated Ruthenium Catalysts for Z-Selective Olefin Metathesis," J. Am. Chem. Soc., 2011, 133, pp. 8525-8527.
Flook et al., "Z-Selective Olefin Metathesis Processes Catalyzed by a Molybdenum Hexaisopropylterphenoxide Monopyrrolide Complex," J. Am. Chem. Soc., 2009, 131, pp. 7962-7963.
Gusev et al., "Alkylidene and Vinylidene "Pincer" Complexes from Reactions of Alkynes with Ruthenium and Osmium Hydrides," Organometallics, vol. 21, No. 6, 2002, pp. 1095-1100.
Jafarpour et al., "Improved One-Pot Synthesis of Second-Generation Ruthenium Olefin Metathesis Catalysts," Organometallics, vol. 21, No. 2., 2002, pp. 442-444.
Jazzar et al., "C-C and C-H Bond Activation Reactions in N-Heterocyclic Carbene Complexes of Ruthenium," J. Am. Chem. Soc., 2002, 124, pp. 4944-4945.
Keitz et al., "Z-Selective Homodimerization of Terminal Olefins with a Ruthenium Metathesis Catalyst," J. Am. Chem. Soc., 2011, 133, pp. 9686-9688.
Keitz et al., "Cis-Selective Ring-Opening Metathesis Polymerization with Ruthenium Catalysts," J. Am. Chem. Soc., 2012, 134, pp. 2040-2043.
Krause et al., "Synthesis and Reactivity of Homongeneous and Heterogeneous Ruthenium-Based Metathesis Catalysts Containing Electron-Withdrawing Ligands," Chem. Eur. J. 2004, 10, pp. 777-784.
Paczal et al., "Modular Synthesis of Heterocyclic Carbene Precursors," J. Org. Chem. 2006, 71, pp. 5969-5979.
Pangborn et al., "Safe and Convenient Procedure for Solvent Purification," Organometallics, 1996, 15, pp. 1518-1520.
Rosen et al., "Olefin Metathesis Catalysts Containing Acyclic Diaminocarbenes," Organometallics, 2010, 29, pp. 250-256.
Samojlowicz et al., "Ruthenium-Based Olefin Metathesis Catalysts Bearing N-Heterocyclic Carbene Ligands," Chem. Rev. 2009, 109, pp. 3708-3742.
Teo et al., "Facile Synthesis of Efficient and Selective Ruthenium Olefin Metathesis Catalysts with Sulfonate and Phosphate Ligands," Organometallics, 2010, 29, pp. 6045-6050.

* cited by examiner

Z-SELECTIVE METATHESIS CATALYSTS

RELATED APPLICATIONS

This application claims the benefit of priority to U.S. Provisional Application Ser. No. 61/736,443 (CIT-6312-P2), filed Dec. 12, 2012, the contents of which is incorporated herein by reference.

STATEMENT OF FEDERAL SUPPORT

This invention was made with government support under GM031332 awarded by the National Institutes of Health and under CHE1048404 awarded by the National Science Foundation. The government has certain rights in the invention.

TECHNICAL FIELD

This invention relates generally to C—H activated metathesis catalysts, to the preparation of such catalysts, and the use of such catalysts in the metathesis of olefins and olefin compounds, more particularly, in the use of such catalysts in Z-selective olefin metathesis reactions. The invention has utility in the fields of organometallics, polymer chemistry, and organic synthesis.

BACKGROUND

The transition-metal catalyzed olefin metathesis reaction has emerged as an indispensable methodology for the construction of new carbon-carbon double bonds (see (a) Fürstner, A. *Angew. Chem., Int. Ed.* 2000, 39, 3013. (b) Trnka, T. M.; Grubbs, R. H. *Acc. Chem. Res.* 2001, 34, 18. (c) Schrock, R. R. *Chem. Rev.* 2002, 102, 145. (d) Schrock, R. R.; Hoveyda, A. H. *Angew. Chem., Int. Ed.* 2003, 42, 4592. (e) Vougioukalakis, G.; Grubbs, R. H. *Chem. Rev.* 2009, 110, 1746. (f) Samojlowicz, C.; Bieniek, M.; Grela, K. *Chem. Rev.* 2009, 109, 3708). Since its discovery in the 1950s, metathesis has been employed with great success in a number of fields, including biochemistry, materials science, and green chemistry (see (a) Binder, J. B.; Raines, R. T. *Curr. Opin. Chem. Biol.* 2008, 12, 767; (b) Leitgeb, A.; Wappel, J.; Slugovc, C. *Polymer* 2010, 51, 2927; (c) Sutthasupa, S.; Shiotsuki, M.; Sanda, F. *Polym. J.* 2010, 42, 905; (d) Liu, X.; Basu, A. *J. Organomet. Chem.* 2006, 691, 5148; (e) Schrodi, Y.; Ung, T.; Vargas, A.; Mkrtumyan, G.; Lee, C. W.; Champagne, T. M.; Pederson, R. L.; Hong, S. H. *CLEAN Soil, Air, Water* 2008, 36, 669). However, an ongoing challenge in cross metathesis (CM) reactions has been the control of stereoselectivity, as metathesis catalysts generally favor formation of the thermodynamically preferred E-olefin (see Grubbs, R. H. *Handbook of Metathesis;* Wiley-VCH: Weinheim, 2003). Many natural products and pharmaceutical targets, on the other hand, contain Z-olefins (see Cossy, J.; Arseniyadis, S.; Meyer, C. *Metathesis in Natural Product Synthesis: Strategies, Substrates, and Catalysts,* 1st ed.; Wiley-VCH: Weinheim, Germany, 2010). Recent groundbreaking work by Schrock and Hoveyda et. al. resulted in the development of the first Z-selective metathesis catalysts using molybdenum and tungsten, allowing for the effective synthesis of Z-olefins via metathesis for the first time and opening the door to the development of new and improved Z-selective catalysts (see (a) Flook, M. M.; Jiang, A. J.; Schrock, R. R.; Müller, P.; Hoveyda, A. H. *J. Am. Chem. Soc.* 2009, 131, 7962. (b) Marinescu, S. C.; Schrock, R. R.; Müller, P.; Takase, M. K.; Hoveyda, A. H. *Organometallics* 2011, 30, 1780. (c) Yu, M.; Wang, C.; Kyle, A. F.; Jukubec, P.; Dixon, D. J.; Schrock, R. R.; Hoveyda, A. H. *Nature* 2011, 479, 88. (d) Meek, S. J.; O'Brien, R. V.; Llaveria, J.; Schrock, R. R.; Hoveyda, A. H. *Nature* 2011, 471, 461. (e) Flook, M. M.; Ng, V. W. L.; Schrock, R. R. *J. Am. Chem. Soc.* 2011, 133, 1784. (f) Jiang, A. J.; Zhao, Y.; Schrock, R. R.; Hoveyda, A. H. *J. Am. Chem. Soc.* 2009, 131, 16630).

More recently, we reported on the synthesis and activity of a comparable class of Z-selective ruthenium metathesis catalysts (2, 3) containing a chelating N-heterocyclic carbene (NHC) ligand (Scheme 1) (see (a) Endo, K.; Grubbs, R. H. *J. Am. Chem. Soc.* 2011, 133, 8525. (b) Keitz, B. K.; Endo, K.; Herbert, M. B.; Grubbs, R. H. *J. Am. Chem. Soc.* 2011, 133, 9686. (c) Keitz, B. K.; Endo, K.; Patel, P. R.; Herbert, M. B.; Grubbs, R. H. *J. Am. Chem. Soc.* 2011, 134, 693). The Z-selective ruthenium-based metathesis catalyst, nitrato-catalyst 3, was found to possess turnover numbers (TONs) approaching 1000 and Z-selectivity on average around 90%. This catalyst has been shown to be effective for the synthesis of homo- and heterocross products, stereoregular polymers, and a variety of insect pheromones and macrocyclic musks (see (a) Keitz, B. K.; Endo, K.; Patel, P. R.; Herbert, M. B.; Grubbs, R. H. *J. Am. Chem. Soc.* 2011, 134, 693. (b) Keitz, B. K.; Fedorov, A.; Grubbs, R. H. *J. Am. Chem. Soc.* 2012, 134, 2040. (c) Herbert, M. B.; Marx, V. M.; Pederson, R. L.; Grubbs, R. H. DOI: 10.1002/anie.201206079. (d) Marx, V. M.; Herbert, M. B.; Keitz, B. K.; Grubbs, R. H. Unpublished results).

Scheme 1. Synthetic Route to Previously Reported C—H Activated Methathesis Catalysts.

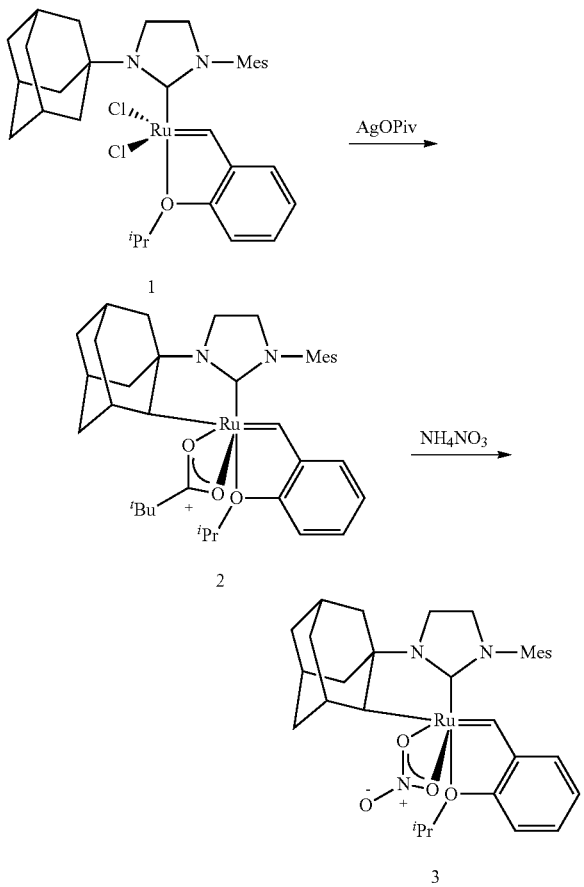

The Ru—C bond of the chelate in 2 and 3 is formed via an intramolecular C—H activation of an N-bound adamantyl group induced by the addition of silver pivalate (AgOPiv) (Scheme 1). Past experience with similarly activated complexes, combined with computational data, suggested that replacing the mesityl group of compound 3 with a N-2,6-diisopropylphenyl (DIPP) group would result in increased catalyst stability and selectivity. As detailed in a previous report, attempts to make significant alterations to the NHC substituents, both to the chelating group and to the N-aryl group, mostly resulted in decomposition upon exposure to AgOPiv (see Herbert, M. B.; Lan, Y.; Keitz, B. K.; Liu, P.; Endo, K.; Day, M. W.; Houk, K. N.; Grubbs, R. H. *J. Am. Chem. Soc.* 2012, 134, 7861).

Despite the advances achieved in preparing Z-selective metathesis catalysts, a continuing need in the art exists for improved catalysts, particularly Z-selective metathesis catalysts that provide higher turnover numbers (TONs) and improved Z-selectivity as well as improved methods for making such catalysts.

BRIEF SUMMARY OF THE DISCLOSURE

The invention is directed to addressing one or more of the aforementioned concerns, and, in one embodiment of the invention provides a C—H activated metathesis catalyst represented by the formula 8,

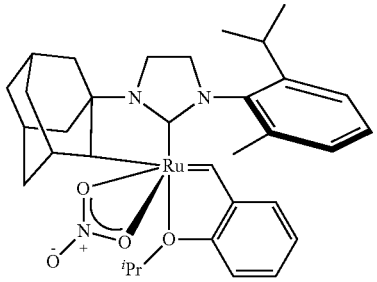

8

Another embodiment of the invention provides a method for preparing the C—H activated metathesis catalyst represented by the formula 8, comprising adding sodium pivalate with a metathesis catalyst represented by the formula S10

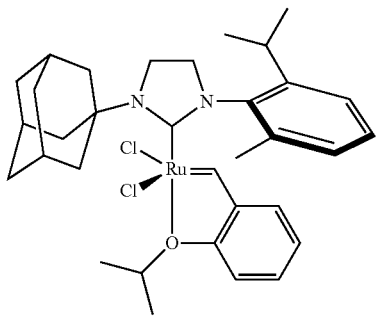

S10 to form a reaction mixture, and subsequently adding ammonium nitrate to the reaction mixture.

Another embodiment of the invention provides a C—H activated metathesis catalyst represented by the formula 9,

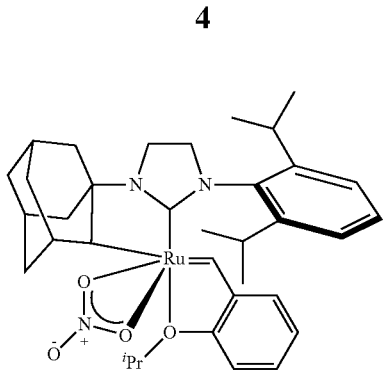

9

Another embodiment of the invention provides a method for preparing the C—H activated metathesis catalyst represented by the formula 9, comprising adding sodium pivalate with a metathesis catalyst represented by the formula 4

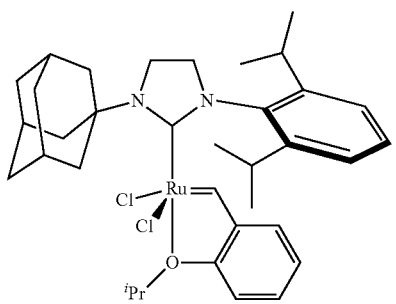

4 to form a reaction mixture, and subsequently adding ammonium nitrate to the reaction mixture.

Another embodiment of the invention provides a C—H activated metathesis catalyst represented by the formula 6,

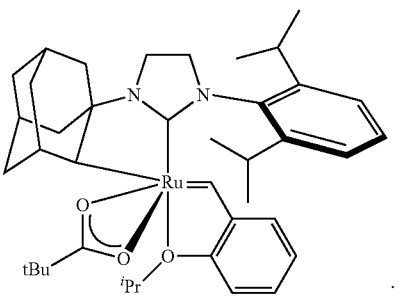

6

In another embodiment, the invention provides a method of making a C—H activated catalyst represented by the formula 6, the method comprising adding sodium pivalate with a metathesis catalyst represented by the formula 4.

In another embodiment, the invention provides for use of a C—H activated metathesis catalyst for ring closing metathesis, cross metathesis, homodimerization, or ring opening metathesis polymerization, wherein the C—H activated metathesis catalyst is represented by the formula 8.

In another embodiment, the invention provides for use of a C—H activated metathesis catalyst for ring closing metathesis, cross metathesis, homodimerization, or ring opening metathesis polymerization, wherein the C—H activated metathesis catalyst is represented by the formula 9.

In another embodiment, the invention provides for use of a C—H activated metathesis catalyst for ring closing metathesis, cross metathesis, homodimerization, or ring opening metathesis polymerization, wherein the C—H activated metathesis catalyst is represented by the formula 6.

In another embodiment, the invention provides a process for cross metathesis comprising the use of a C—H activated metathesis catalyst represented by the formula 8.

In another embodiment, the invention provides a process for cross metathesis comprising the use of a C—H activated metathesis catalyst represented by the formula 9.

In another embodiment, the invention provides a process for cross metathesis comprising the use of a C—H activated metathesis catalyst represented by the formula 6.

In another embodiment, the invention provides a process for ring closing metathesis comprising the use of a C—H activated metathesis catalyst represented by the formula 8.

In another embodiment, the invention provides a process for ring closing metathesis comprising the use of a C—H activated metathesis catalyst represented by the formula 9.

In another embodiment, the invention provides a process for ring closing metathesis comprising the use of a C—H activated metathesis catalyst represented by the formula 6.

In another embodiment, the invention provides a process for ring opening metathesis polymerization comprising the use of a C—H activated metathesis catalyst represented by the formula 8.

In another embodiment, the invention provides a process for ring opening metathesis polymerization comprising the use of a C—H activated metathesis catalyst represented by the formula 9.

In another embodiment, the invention provides a process for ring opening metathesis polymerization comprising the use of a C—H activated metathesis catalyst represented by the formula 6.

In another embodiment, the invention provides a process for preparing a pheromone compound comprising the use of a C—H activated metathesis catalyst selected from catalyst 6, catalyst 8, or catalyst 9.

In another embodiment, the invention provides a process for preparing a pheromone compound comprising the use of a C—H activated metathesis catalyst selected form catalyst 6, catalyst 8, or catalyst 9, wherein the pheromone compound is represented by compound 17.

In another embodiment, the invention provides a process for preparing a pheromone compound comprising the use of a C—H activated metathesis catalyst represented by formula 9, wherein the pheromone compound is represented by the formula 17.

In another embodiment, the invention provides a process for preparing a pheromone compound comprising combining 1-hexene and 8-nonenyl acetate to form a reaction mixture, and adding a C—H activated metathesis catalyst according to claim 2 to the reaction mixture, wherein the pheromone compound is represented by the formula 17

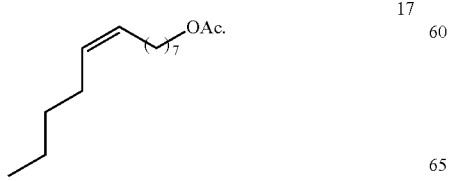

In another embodiment, the invention provides a process for preparing a pheromone compound comprising combining 1-hexene and 8-nonenyl acetate to form a reaction mixture, and adding a C—H activated metathesis catalyst selected from catalyst 6, catalyst 8, or catalyst 9 to the reaction mixture, wherein the pheromone compound is represented by compound 17.

In another embodiment, the invention provides a process for preparing a macrocyclic compound comprising reacting a C—H activated metathesis catalyst according to claim 2 with a diene, wherein the diene is represented by the formula 18a

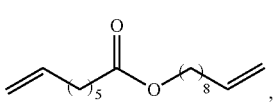

and the macrocyclic compound is represented by the formula 18

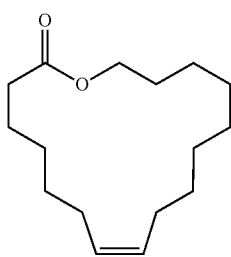

In another embodiment, the invention provides a process for preparing a macrocyclic compound comprising reacting a C—H activated metathesis catalyst according to claim 2 with a diene, wherein the diene is represented by the formula 19a

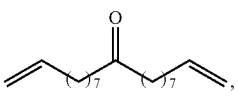

and the macrocyclic compound is represented by the formula 19

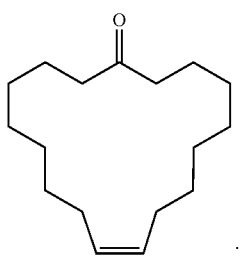

In another embodiment, the invention provides a process for preparing a macrocyclic compound comprising reacting a C—H activated metathesis catalyst selected from catalyst 6, catalyst 8, or catalyst 9 with a diene.

process for preparing a macrocyclic compound comprising reacting a C—H activated metathesis catalyst according to claim 2 with a diene, wherein the diene is represented by the formula 20 a

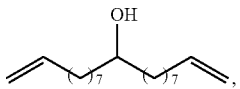

and the macrocyclic compound is represented by the formula 20

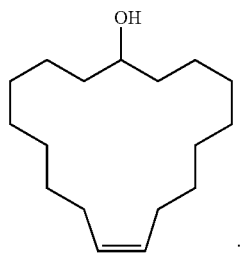

In another embodiment, the invention provides a process for preparing a macrocyclic compound comprising reacting a C—H activated metathesis catalyst selected from catalyst 6, catalyst 8, or catalyst 9 with a diene.

In another embodiment, the invention provides a process for preparing a macrocyclic compound comprising reacting a C—H activated metathesis catalyst selected from catalyst 6, catalyst 8, or catalyst 9 with a diene, wherein the diene is represented by the formula 18a, and the macrocyclic compound is represented by the formula 18.

In another embodiment, the invention provides a process for preparing a macrocyclic compound comprising reacting a C—H activated metathesis catalyst selected from catalyst 6, catalyst 8, or catalyst 9 with a diene, wherein the diene is represented by the formula 19a, and the macrocyclic compound is represented by the formula 19.

In another embodiment, the invention provides a process for preparing a macrocyclic compound comprising reacting a C—H activated metathesis catalyst selected from catalyst 6, catalyst 8, or catalyst 9 with a diene, wherein the diene is represented by the formula 20a, and the macrocyclic compound is represented by the formula 20.

In another embodiment, the invention provides a process for homodimerization comprising the use of a C—H activated metathesis catalyst selected from catalyst 6, catalyst 8, or catalyst 9.

In another embodiment, the invention provides a process for homodimerization comprising the use of a C—H activated metathesis catalyst represented by formula 6.

In another embodiment, the invention provides a process for homodimerization comprising the use of a C—H activated metathesis catalyst represented by formula 8.

In another embodiment, the invention provides a process for homodimerization comprising the use of a C—H activated metathesis catalyst represented by formula 9.

These and other aspects of the invention will be apparent to the skilled artisan in light of the following detailed description and examples.

DETAILED DESCRIPTION OF THE DISCLOSURE

Unless otherwise indicated, the invention is not limited to specific reactants, substituents, catalysts, resin compositions, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, including the foregoing molecular structures and formulae, Ph represents phenyl, Me represents methyl, $^t$Bu represents tent-butyl, $^i$Pr represents isopropyl, OAc represents $CH_3$—C(=O)—O—, Mes represents mesityl (i.e., 2,4,6-trimethylphenyl), DIPP represents 2,6-diisopropylphenyl, and MIPP respresents 2-isopropylphenyl.

In order to access stable chelated species with various modifications to the NHC substituents, we sought to develop a milder approach to form this ruthenium-carbon bond. Herein, we report on an improved method to induce the salt metathesis and C—H activation of ruthenium alkylidene complexes employing mild and economically viable sodium carboxylates, and explore the superior activity and selectivity of several new chelated metathesis-active catalysts. Using this approach, we have synthesized a number of previously inaccessible catalytically-active species, including a derivative bearing an N-2,6-diisopropylphenyl group on the NHC ligand that shows significant improvements in selectivity and activity for a number of homodimerization and industrially-relevant reactions over the previous leading ruthenium-based Z-selective metathesis catalyst. Through the use of this improved approach, we have uncovered the highly active catalyst 9, which on average gives >95% Z-selectivity and TONs of up to 7400 in the homodimerizations of terminal olefin substrates. In contrast, recently reported molybdenum- and tungsten-based systems reach TONs of up to 500 with comparable Z-selectivities for the same reactions (see Peryshkov, D. V.; Schrock, R. R.; Takase, M. K.; Muller, P.; Hoveyda, A. H. J. Am. Chem. Soc. 2011, 133, 2075). As such, the turnover numbers reported herein are the highest for any Z-selective metathesis catalyst to date. Moreover, we have demonstrated the ability of this new catalyst to form insect pheromones and macrocycles containing a variety of functional groups with consistently impressive selectivity (>95% in all cases) for the Z-isomer. From these studies, important insight was gained into the effects of altering the N-aryl group in this class of catalysts and will enable the development of future generations of Z-selective catalysts. We feel that the results presented here represent a significant improvement in the field of Z-selective metathesis and will allow access to Z-olefin-containing products and materials previously inaccessible via ruthenium-based olefin metathesis. We believe that this work is of broad interest to researchers working in the fields of organometallics, polymer chemistry, and organic synthesis.

Scheme 2. Decomposition and C—H Activation Pathways of 4.

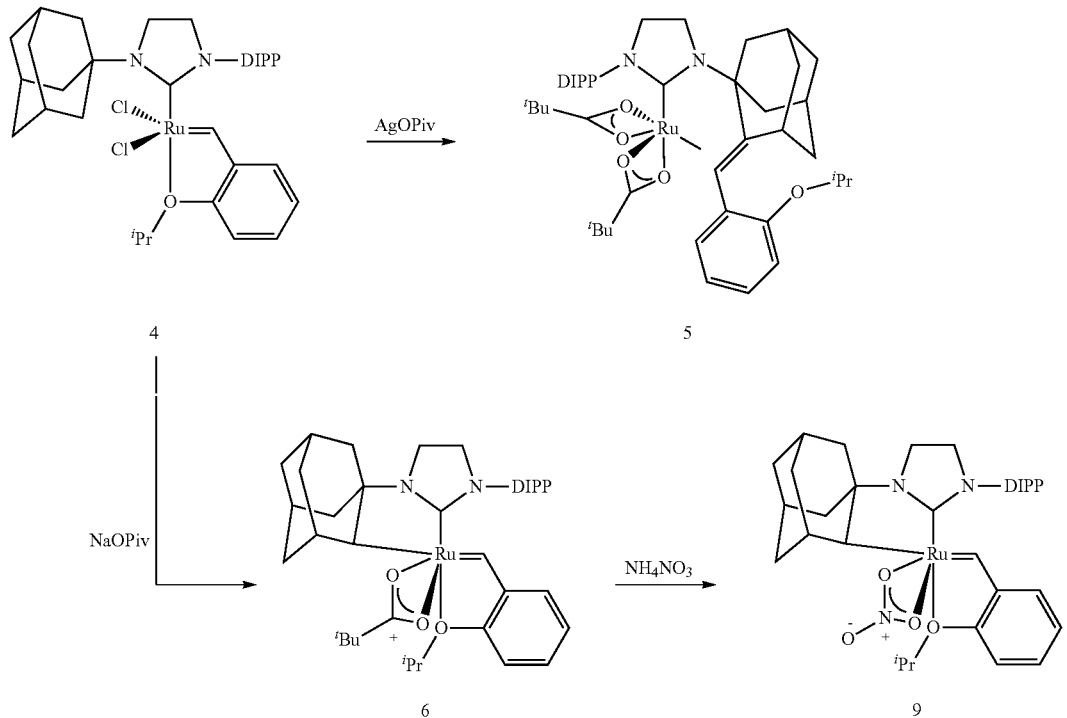

We initiated our studies by first employing sodium pivalate (NaOPiv) in place of AgOPiv during the C—H activation step. It was quickly discovered that exposing the unactivated dichloride catalyst 1 to excess NaOPiv in a 1:1 mixture of THF and MeOH resulted in the clean formation of the desired chelated catalyst 2 after heating at 40° C. for 6 hours. The two-step synthesis of 3 using AgOPiv proceeded in 48% overall yield, whereas the same sequence using NaOPiv provided 3 in 60% overall yield. Reaction of 1 with excess sodium acetate also resulted in complete conversion to 2, but with some catalysts the C—H activation failed to reach full conversion. Reducing the steric bulk of the carboxylate even further by using sodium formate or sodium bicarbonate results in no discernible conversion to the desired chelated product. In order to explore the utility and mildness of this new approach, we revisited a number of ruthenium complexes containing a variety of N-aryl and N-carbocyclic groups that had decomposed when using AgOPiv. Attempts to replace the N-mesityl group of 3 with a bulkier DIPP group, as in 4, for example, had resulted in substantial decomposition to 5 during the C—H activation step. Using NaOPiv, however, we were able to cleanly form the stable N-adamantyl, N-DIPP pivalate precursor (6) of catalyst 9 (Scheme 2).

We were also able to generate activated N-3,5-dimethyladamantyl, N-mesityl (7) and N-adamantyl, N-2,6-methylisopropylphenyl (MIPP) (8) derivatives via this improved method. More extreme alterations to the chelating group, however, including exchanging the N-adamantane for an N-cyclohexyl or N-1-methylcyclohexyl group, resulted in the formation of chelated catalysts that were inherently unstable. When these reactions were monitored by $^1$H NMR spectroscopy, these complexes were seen to either decompose immediately to a ruthenium-hydride species upon introduction of NaOPiv or form a meta-stable activated complex that was unisolable without noticeable decomposition.

Complexes observed to form a stable chelated architecture were subsequently converted to the nitrate form via ligand exchange with the pivalate (Scheme 2), as past experience with catalyst 3 suggested that the nitrato-complexes would be more stable and show increased activity. 6 and the pivalate analogue of catalyst 8 were isolated and assayed. As expected, they exhibited decreased activity and stability compared to the corresponding nitrato-complexes (see Keitz, B. K.; Endo, K.; Patel, P. R.; Herbert, M. B.; Grubbs, R. H. *J. Am. Chem. Soc.* 2011, 134, 693). While this seemed to be the case for complexes possessing a chelating N-adamantyl group, catalyst 7 was more stable and more easily isolated in the pivalate form. Catalysts successfully synthesized using the NaOPiv method are depicted in Figure 1.

FIG. 1. Catalysts 7-9.

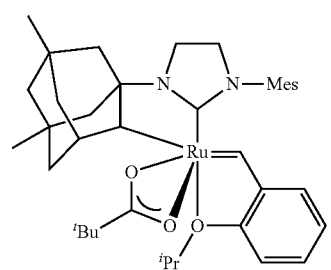

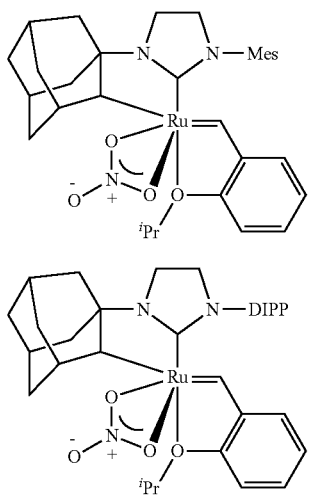

To look at the efficacy of these new complexes for metathesis, we first evaluated their performance in the homodimerization of allyl benzene (10). While a relatively facile substrate for homodimerization, allyl benzene is also prone to olefin isomerization to form 12. Importantly, the extent of this side reaction depends heavily on the identity and stability of the catalyst, making 10 a good benchmark substrate (see Ritter, T.; Hejl, A.; Wenzel, A. G.; Funk, T. W.; Grubbs, R. H. *Organometallics* 2006, 25, 5740). Homodimerization reactions were generally run in THF at 35° C. with a high substrate concentration (3.3 M in 10) and a catalyst loading varying between 0.1 and 2 mol %. Catalyst 8 was not soluble in THF, thus all reactions using 8 were run in 1,2-dichloroethane (DCE). Excellent conversions and near-perfect Z-selectivities (>95%) were seen by $^1$H NMR spectroscopy with 7-9, with 8 and 9 being the most selective for the homodimer 11 over the olefin isomerization product 12.

TABLE 1

Homodimerization of Allyl Benzene (10).

| catalyst | loading, mol % | time, h | conv, %$^a$ | Z-11, %$^a$ | 11/12$^a$ |
|---|---|---|---|---|---|
| 7 | 2 | 1.5 | 94 | >95 | 16.6 |
| 8$^b$ | 0.1 | 2 | 78 | >95 | 50 |
| 9 | 0.1 | 2 | >95 | >95 | 50 |

$^a$Determined by $^1$H NMR spectroscopy.
$^b$DCE was used in place of THF.

In order to differentiate between these very active catalysts, we turned to two more challenging homodimerization substrates, methyl 10-undecenoate (13) and the primary alcohol 4-pentenol (14), the latter of which has been indirectly implicated in the decomposition of previous generations of ruthenium metathesis catalysts (see (a) Trnka, T. M.; Morgan, J. P.; Sanford, M. S.; Wilhelm, T. E.; Scholl, M.; Choi, T. L.; Ding, S.; Day, M. W.; Grubbs, R. H. *J. Am. Chem. Soc.* 2003, 125, 2546. (b) Beach, N. J.; Lummiss, J. A. M.; Bates, J. M.; Fogg, D. E. *Organometallics* 2012, 31, 2349). Reactions were run utilizing the standard conditions described above. Of the three catalysts, 9 gave the best results, providing the homodimerization products in high conversions (>95% and 77% for 13 and 14, respectively) with >95% Z-selectivity for both substrates. Catalyst 8 also demonstrated excellent selectivity (>95% Z for both substrates) but low conversions, particularly in the homodimerization of 14 (7%). The homodimerization of 14 using catalyst 9 in DCE under the standard conditions (3.3M in substrate, 0.1 mol % catalyst loading, 35° C.) gave 67% conversion (>95% Z) after 1 h, and 79% conversion (92% Z) after 2 h. The almost exclusive selectivity for the Z-olefin observed with 8 and 9 is likely a result of the steric bulk of the N-MIPP or N-DIPP group positioned over the alkylidene, which ensures that any approach of the terminal olefin in a manner that would produce an E-olefin is extremely disfavored (see Liu, P.; Xu, X.; Dong, X.; Keitz, B. K.; Herbert, M. B.; Grubbs, R. H.; Houk, K. N. *J. Am. Chem. Soc.* 2012, 134, 1464). Previously, the homodimer of 14 was isolated in 67% yield with only 81% selectivity for the Z-olefin using catalyst 3; thus the development of 9 represents a significant improvement in the field of Z-selective metathesis.

TABLE 2

Homodimerization of 10-Methyl Undecenoate (13) and 4-Pentenol (14).

R = —(CH$_2$)$_8$CO$_2$Me (13),
—(CH$_2$)$_3$OH (14)

| substrate | catalyst | loading, mol % | time, h | conv, %$^a$ | Z, %$^a$ |
|---|---|---|---|---|---|
| 13 | 7 | 2 | 3 | 77 | 91 |
|  | 8$^b$ | 0.1 | 6 | 65 | >95 |
|  | 9 | 0.1 | 6 | >95 | >95 |
| 14 | 7 | 2 | 1.5 | 83 | 80 |
|  | 8$^b$ | 0.1 | 2 | 7 | >95 |
|  | 9 | 0.1 | 2 | 77 | >95 |

$^a$Determined by $^1$H NMR spectroscopy.
$^b$DCE was used in place of THF.

In order to further quantify the activity of the highly Z-selective catalyst 9, we assayed its performance at room temperature and lower concentration (1 M in substrate). Under these conditions, similar conversions and Z-selectivities were observed compared to those recorded under standard conditions, although significantly longer reaction times were necessary. We additionally tested 9 at 0.01 mol % and were pleased to discover that it performed exceptionally well, reaching turnover numbers as high as 5,800 and 7,400 in the homodimerizations of 14 and 10, respectively, while maintaining >95% Z-selectivity. This is in comparison to previously reported TONs of up to 1,000 for catalyst 3 in conjunction with on average 90% Z-selectivity (see Keitz, B. K.; Endo, K.; Patel, P. R.; Herbert, M. B.; Grubbs, R. H. *J. Am. Chem. Soc.* 2011, 134, 693). Finally, isolated yields were obtained for all reactions employing catalyst 9, including those run using the standard conditions (Table S1).

TABLE S1

Isolated Yields for Homodimerizations Using Catalyst 9.

| substrate | loading, mol % | conc., M | temp, °C | time, h | isolated yield, % | Z, % | TON |
|---|---|---|---|---|---|---|---|
| 10 | 0.1 | 3.3 | 35 | 2 | 84 | >95 | 840 |
|  | 0.1 | 1 | 23 | 6.5 | 91 | >95 | 910 |
|  | 0.01 | 7[b] | 35 | 2.5 | 74 | >95 | 7400 |
| 13 | 0.1 | 3.3 | 35 | 6.5 | 87 | >95 | 870 |
|  | 0.1 | 1 | 23 | 12 | 85 | >95 | 850 |
|  | 0.01 | 3.3 | 35 | 12 | 58 | >95 | 5800 |
| 14 | 0.1 | 3.3 | 35 | 2.5 | 81 | >95 | 810 |
|  | 0.1 | 1 | 23 | 12 | 80 | >95 | 800 |
|  | 0.01 | 3.3 | 35 | 4.5 | 15 | >95 | 1500 |

[a]Determined by ¹H NMR spectroscopy.
[b]Run at a higher substrate concentration to increase catalyst initiation and activity. Due to insufficient solubility of 9 in 13 and 14, however, homodimerizations of those substrates at 0.01 mol % were run at the maximum concentration achievable (3.3M).

Having established the effectiveness of 9 in homodimerization reactions, we set about to further evaluate its activity and Z-selectivity by exploring more complex transformations. The reaction of 1-hexene (15) and 8-nonenyl acetate (16) to form the pheromone derivative 17 was previously described using catalyst 3, and proceeded in good yield (67%) with high Z-selectivity (91%) at a low catalyst loading (0.5 mol %) (see Keitz, B. K.; Endo, K.; Patel, P. R.; Herbert, M. B.; Grubbs, R. H. *J. Am. Chem. Soc.* 2011, 134, 693). Catalyst 9 was able to catalyze this transformation with no observable formation of the E-isomer and in slightly higher yield (71%) at the same catalyst loading. Additionally, the catalyst loading could be lowered to 0.1 mol % and still provide a good yield of 17 (60%) while maintaining >95% Z-selectivity (Scheme 3). The expansion of this methodology to produce more complicated cross products with presumably total Z-selectivity should further enable its widespread use in the synthesis of Z-olefin-containing pheromones and other natural products.

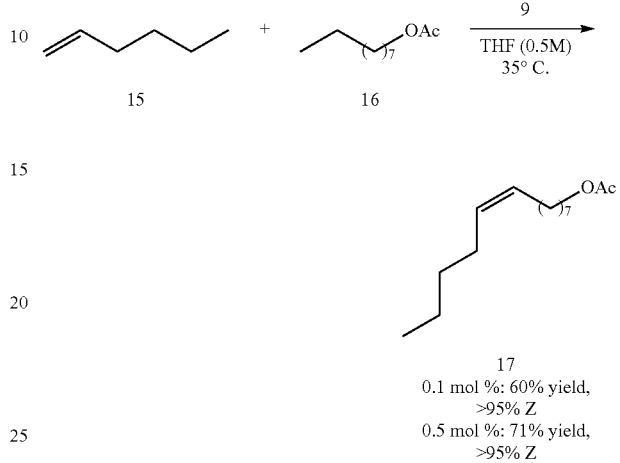

Scheme 3. Synthesis of Pheromone 17 Using Catalyst 9.

17
0.1 mol %: 60% yield, >95% Z
0.5 mol %: 71% yield, >95% Z

We next evaluated catalyst 9 in macrocyclic ring-closing metathesis (RCM) (see (a) Grubbs, R. H. *Handbook of Metathesis;* Wiley-VCH: Weinheim, 2003. (b) Cossy, J.; Arseniyadis, S.; Meyer, C. *Metathesis in Natural Product Synthesis: Strategies, Substrates, and Catalysts,* 1st ed.; Wiley-VCH: Weinheim, Germany, 2010. (c) Gradillas, A.; Pérez-Castells, J. *Angew. Chem. Int. Ed.* 2006, 45, 6086-6101. (d) Majumdar, K. C.; Rahaman, H.; Roy, B. *Curr. Org. Chem.* 2007, 11, 1339-1365. (e) Diederich, F.; Stang, P. J.; Tykwinski, R. R. *Modern Supramolecular Chemistry: Strat-*

TABLE 3

Z-Selective Macrocyclizations Employing Catalyst 9.[a]

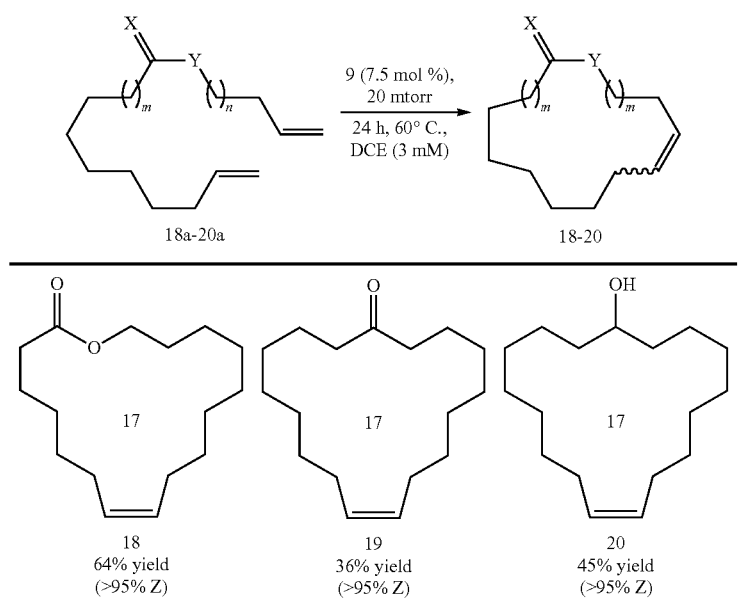

18
64% yield
(>95% Z)

19
36% yield
(>95% Z)

20
45% yield
(>95% Z)

[a]Isolated yields (E/Z ratios determined by ¹H- or ¹³C-NMR spectroscopy).

egies for Macrocycle Synthesis. Wiley-VCH: Weinhem, 2008). Although W- and Mo-based systems exhibit Z-selectivities as high as 97% for these reactions (see Yu, M.; Wang, C.; Kyle, A. F.; Jakubec, P.; Dixon, D. J.; Schrock, R. R.; Hoveyda, A. H. Nature. 2011, 479, 88-93) the Ru-based systems on average only result in ca. 85% Z-selectivity (see Marx, V. M.; Herbert, M. B.; Keitz, B. K.; Grubbs, R. H. Unpublished results). Particularly problematic for the Ru-based system are substrates containing ketone or alcohol functionality, in which it is observed that the Z-isomer is readily degraded at high conversions. Thus, we were delighted to find that when dienes 18a-20a were exposed to catalyst 9, macrocycles 18-20 were all obtained in modest yields and with only trace amounts of the E-isomer evident by $^1$H and $^{13}$C NMR spectroscopy (Table 3). It is expected that this methodology will have application to a variety of natural products and pharmaceuticals, as well as for the synthesis of a unique class of olfactory compounds, termed macrocyclic musks. Many of these compounds contain a macrocyclic backbone either featuring a Z-olefin, or bearing functionality stereospecifically installed using a Z-olefin (see (a) Grubbs, R. H. Handbook of Metathesis; Wiley-VCH: Weinheim, 2003. (b) Cossy, J.; Arseniyadis, S.; Meyer, C. Metathesis in Natural Product Synthesis: Strategies, Substrates, and Catalysts, 1st ed.; Wiley-VCH: Weinheim, Germany, 2010. (c) Gradillas, A.; Pérez-Castells, J. Angew. Chem. Int. Ed. 2006, 45, 6086-6101. (d) Majumdar, K. C.; Rahaman, H.; Roy, B. Curr. Org. Chem. 2007, 11, 1339-1365. (e) Diederich, F.; Stang, P. J.; Tykwinski, R. R. Modern Supramolecular Chemistry: Strategies for Macrocycle Synthesis. Wiley-VCH: Weinhem, 2008. (f) Rowe, D. J. Chemistry and Technology of Flavors and Fragrances. Blackwell: Oxford, 2005. (g) Ohloff, G.; Pickenhagen, W.; Kraft, P. Scent and Chemistry—The Molecular World of Odors. Verlag Helvectica Acta: Zurich, 2011). In fact, 18 and 19 are both currently in demand by the perfume industry (marketed as ambrettolide and civetone, respectively) (see (a) Rowe, D. J. Chemistry and Technology of Flavors and Fragrances. Blackwell: Oxford, 2005. (b) Ohloff, G.; Pickenhagen, W.; Kraft, P. Scent and Chemistry—The Molecular World of Odors. Verlag Helvectica Acta: Zurich, 2011).

In summary, we have developed a new method to effect the salt metathesis and C—H activation of Z-selective ruthenium-based metathesis catalysts using sodium carboxylates. This approach has been used to synthesize several new stable chelated species, all of which were found to be Z-selective in the homodimerizations of terminal olefin substrates. Notably, installation of an N-2,6-diisopropylphenyl group on the NHC led to significant improvements in activity and selectivity in both the homodimerization reactions of terminal olefins and industrially relevant products. Near-perfect selectivity for the Z-olefin (>95%) and unmatched TONs of up to 7,400 were observed while retaining the ease of use associated with the ruthenium family of metathesis catalysts.

EXPERIMENTAL

General Information

In the following examples, efforts have been made to insure accuracy with respect to numbers used (e.g., amounts, temperature, etc.) but some experimental error and deviation should be accounted for. The following examples are to be considered as not being limiting of the invention as described herein, and are instead provided as representative examples of the invention and the methods of their use.

All reactions were carried out in dry glassware under an argon atmosphere using standard Schlenk techniques or in a Vacuum Atmospheres Glovebox under a nitrogen atmosphere, unless otherwise specified. All solvents were purified by passage through solvent purification columns and further degassed by bubbling argon. $C_6D_6$ was purified by passage through a solvent purification column. $CDCl_3$ and $CD_2Cl_2$ were used as received. All substrates for olefin cross-metathesis (10, 13, and 14) were degassed with argon and filtered through a plug of neutral alumina prior to use. $RuCl_2(PCy_3)(=CH-o-O^iPrC_6H_4)$ (S4) was obtained from Materia, Inc. 4 was synthesized according to the literature procedure (see Herbert, M. B.; Lan, Y.; Keitz, B. K.; Liu, P.; Endo, K.; Day, M. W.; Houk, K. N.; Grubbs, R. H. J. Am. Chem. Soc. 2012, 134, 7861). Other commercially available reagents and silica gel were used as received.

$^1$H NMR spectra were acquired at 400 or 500 MHz and $^{13}$C NMR spectra at 101 or 126 MHz as $CDCl_3$ or $C_6D_6$ solutions unless otherwise noted. Chemical shifts are reported in ppm downfield from $Me_4Si$ by using the residual solvent peak as an internal standard. Spectra were analyzed and processed using MestReNova Ver. 7.1.

High-resolution mass spectra (HRMS) were provided by the California Institute of Technology Mass Spectrometry Facility using a JEOL JMS-600H High Resolution Mass Spectrometer. All HRMS were by positive-ion EI or FAB.

EXAMPLES

Example 1

Preparation of Compound S1

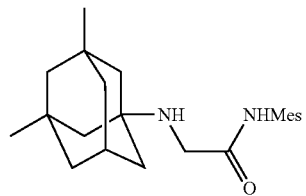

A 3-neck 250 mL RB flask equipped with a condenser was flame dried and charged with 2-chloro-N-mesitylacetamide (3.5 g, 17 mmol), memantine hydrochloride (3.0 g, 14 mmol, OChem Incorp.), and $K_2CO_3$ (4.8 g, 35 mmol). MeCN (110 mL) was added and the suspension was heated to 100° C. under an argon atmosphere for 24 h. After cooling to RT, the mixture was filtered through celite, washing with $CH_2Cl_2$, and the filtrate was concentrated to a white powder. The crude mixture was dry loaded onto a silica gel column and purified via flash chromatography using $Et_2O$ as eluant to give S1 (3.0 g, 60%) as a white powder. $^1$H NMR (400 MHz, $CDCl_3$) δ 8.97 (br s, 1H), 6.88 (s, 2H), 3.38 (s, 2H), 2.26 (s, 3H), 2.18 (s, 6H), 2.17 (m, 1H), 1.53 (br s, 1H), 1.49 (br d, J=3.2 Hz, 2H), 1.31-1.27 (m, 8H), 1.14 (br q, J=11.6 Hz, 2H), 0.86 (s, 6H). $^{13}$C NMR (101 MHz, $CDCl_3$) δ 171.5, 136.4, 134.7, 131.4, 128.8, 52.8, 50.7, 49.0, 44.3, 42.8, 41.3, 32.4, 30.2, 30.1, 20.9, 18.5. HRMS (FAB+): Calculated—355.2749, Found—355.2766.

Example 2

Preparation of Compound S2

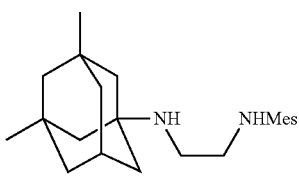

S2

A 2-neck 100 mL RB flask equipped with a condenser was dried and charged with LiAlH$_4$ (1.3 g, 34 mmol) while a separate 25 mL RB flask was dried and charged with Si (3.0 g, 8.4 mmol). THF (50 mL) was added to the LiAlH$_4$ while S1 was dissolved in THF (20 mL) and added dropwise to the LiAlH$_4$ suspension. After the addition was complete, the suspension was heated to 80° C. for 24 h, after which it was cooled to RT and carefully quenched via the dropwise addition of H$_2$O (1.3 mL), 15% NaOH solution (1.3 mL), and H$_2$O (4.0 mL). The quenched reaction was stirred for 5 h under air and filtered through celite, washing with Et$_2$O. The filtrate was concentrated to give S2 (2.8 g, 98%), which was used without further purification. $^1$H NMR (400 MHz, CDCl$_3$) δ 6.86 (s, 2H), 3.04 (t, J=4.4 Hz, 2H), 2.85 (t, J=4.8 Hz, 2H), 2.34 (s, 6H), 2.28 (s, 3H), 2.20 (br s, 1H), 1.55 (s, 2H), 1.38-1.32 (m, 8H), 1.19-1.17 (m, 2H), 0.92 (s, 6H). $^{13}$C NMR (101 MHz, CDCl$_3$) δ 144.0, 130.6, 129.4, 129.2, 52.1, 51.0, 49.5, 49.2, 43.1, 41.4, 40.9, 32.4, 30.4, 30.3, 20.6, 18.6. HRMS (FAB+): Calculated—341.2957, Found—341.2964.

Example 3

Preparation of Compound S3

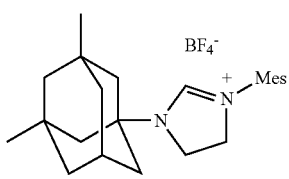

S3

A 100 mL RB flask was dried and charged with S2 (1.0 g, 2.9 mmol), NH$_4$BF$_4$ (0.34 g, 3.2 mmol), and CH(OMe)$_3$ (6.0 mL, 28 mmol). The solution was heated to 100° C. for 4 h, cooled to RT and concentrated. The resulting orange-red residue was washed with cold $^n$BuOH:Toluene (1:1) to give a white precipitate that was collected by filtration. Drying the precipitate under vacuum gave S3 (0.49 g, 44%) as an off-white solid. $^1$H NMR (400 MHz, CDCl$_3$) δ 7.83 (s, 1H), 6.89 (s, 2H), 4.31-4.13 (m, 4H), 2.27 (m, 1H), 2.26 (s, 3H), 2.22 (s, 6H), 1.65 (br s, 2H), 1.61 (br q, J=11.6 Hz, 4H), 1.36 (br q, J=14.4 Hz, 4H), 1.21 (br s, 2H), 0.91 (s, 6H). $^{13}$C NMR (101 MHz, CDCl$_3$) δ 154.7, 139.9, 135.2, 130.7, 129.6, 59.3, 50.4, 49.6, 46.3, 44.9, 41.6, 39.0, 32.6, 29.7, 29.4, 20.8, 17.4. HRMS (FAB+): Calculated—351.2800, Found—351.2755.

Example 4

Preparation of Catalyst S5

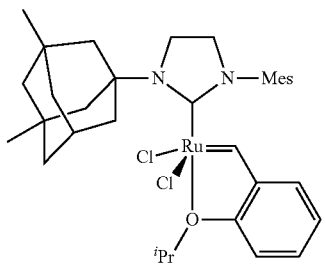

S5

In a glovebox, a solution of S3 (0.49 g, 1.1 mmol) in hexanes (30 mL) was treated with KCOMe$_2$Et (0.14 g, 0.91 mmol), and the mixture was allowed to stir at 35° C. for 1.5 h. To the reaction mixture was then added S4 (0.64 g, 1.1 mmol), upon which the mixture was removed from the glove box and allowed to stir at 65° C. for 3.5 h. The precipitated solids were filtered and washed well with warm hexanes and pentane to give S5 as a green powder: $^1$H NMR (500 MHz, CDCl$_3$) δ 16.90 (s, 1H), 7.55 (ddd, J=8.8, 7.3, 1.9 Hz, 1H), 7.06 (s, 2H), 6.95-6.88 (m, 2H), 6.86 (dd, J=7.5, 1.8 Hz, 1H), 5.09 (hept, J=6.3 Hz, 1H), 4.12 (s, 2H), 4.06-3.98 (m, 2H), 3.90-3.82 (m, 2H), 2.70 (p, J=3.1 Hz, 1H), 2.46 (s, 3H), 2.25 (s, 6H), 2.04 (dd, J=11.9, 1.8 Hz, 2H), 1.81 (d, J=12.2 Hz, 2H), 1.74 (dt, J=12.6, 2.8 Hz, 2H), 1.63 (d, J=6.1 Hz, 6H), 1.47 (dt, J=12.6, 2.4 Hz, 2H), 1.31-1.17 (m, 2H), 0.97 (s, 6H). $^{13}$C NMR (126 MHz, CDCl$_3$) δ 312.4, 207.8, 152.4, 145.9, 139.6, 138.5, 138.1, 130.8, 129.8, 123.9, 122.8, 113.5, 74.4, 58.9, 51.2, 50.7, 47.3, 44.7, 42.4, 42.2, 33.0, 31.3, 30.4, 22.6, 21.3, 18.5. HRMS (FAB+): Calculated—670.2031, Found—670.2028.

Example 5

Preparation of Catalyst 7

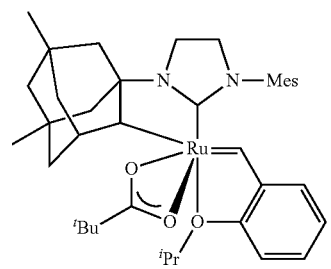

7

In a glovebox, a 20 ml scintillation vial was charged with S5 (0.10 g, 0.16 mmol), NaOPiv (0.19 g, 1.5 mmol), THF (2.0 mL), and MeOH (2.0 mL). The vial was capped, removed from the glovebox, and heated to 40° C. for 4.5 h at which point a color change from green to brown to dark purple was observed. The vial was returned to the box, where the solvent was removed under high vacuum and the residue dissolved in CH$_2$Cl$_2$ (15 mL), filtered through celite, and concentrated to a deep purple residue. The residue was recrystallized from Et$_2$O at −35° C. The resulting crystals were washed with cold Et$_2$O (3×5 mL) to give 7 as a bright purple solid (20 mg, 18%). $^1$H NMR (400 MHz, C$_6$D$_6$) δ 14.83 (s, 1H), 7.46 (dd, J=7.2, 1.6 Hz, 1H), 7.26 (t, J=7.6 Hz, 1H), 6.92 (t, J=7.6 Hz, 1H), 6.83 (br s, 1H), 6.76 (br s, 1H), 6.70 (d, J=8.4 Hz, 1H), 4.79 (sept, J=6.8 Hz, 1H), 3.91 (s, 1H), 3.47-3.40 (m, 2H), 3.27-3.14 (m, 2H), 2.57 (br s, 1H), 2.43 (s, 3H), 2.29 (s, 3H), 2.21 (s, 3H), 1.73 (br d, J=11.2 Hz, 1H), 1.60 (br d, J=10.8 Hz, 1H), 1.53-1.51 (m, 4H), 1.43-1.39 (m, 2H), 1.26 (s, 9H), 1.18 (q, J=6.4 Hz, 4H), 1.03 (d, J=9.6 Hz, 1H), 0.89 (br s, 4H), 0.77 (br d, J=12.8 Hz, 1H), 0.67 (br d, J=10.4 Hz, 1H), 0.62 (s, 3H), 0.31 (br d, J=9.6 Hz, 1H). $^{13}$C NMR (101 MHz, C$_6$D$_6$) δ 259.0, 214.9, 154.2, 143.8, 138.0, 137.0, 136.8, 136.5, 129.9, 129.7, 125.6, 123.1, 122.8, 113.9, 74.5, 66.5, 64.1, 52.1, 51.7, 48.8, 46.6, 42.6, 41.3, 39.8, 39.1, 38.6, 33.4, 32.1, 30.8, 30.7, 28.9, 27.8, 21.6, 21.2, 21.0, 19.1, 19.0. HRMS (FAB+): Calculated—700.3178, Found—700.3181.

Example 6

Preparation of Compound S6

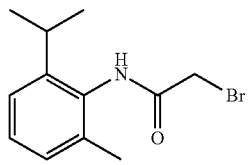

Bromoacetyl chloride (2.8 mL, 34 mmol) was added dropwise to a 0° C. solution of 2-isopropyl-6-methylaniline (5.0 g, 34 mmol) and K$_2$CO$_3$ (9.4 g, 68 mmol) in MeCN (70 mL). The solution was warmed to room temperature, stirred overnight, filtered over celite, and concentrated. Recrystallization from CH$_2$Cl$_2$/hexanes provided S6 (5.5 g, 60%) as a colorless solid. $^1$H NMR δ 7.77 (br s, 1H), 7.24 (m, 1H), 7.18 (m, 1H), 7.11 (m, 1H), 4.08 (s, 2H), 3.06 (m, 1H), 2.24 (s, 3H), 1.21 (d, J=6.9 Hz, 6H). $^{13}$C NMR δ 164.3, 145.7, 135.9, 131.6, 128.4, 123.7, 29.2, 28.7, 23.5, 18.5. HRMS (FAB+): Calculated—270.0493, Found—270.0480.

Example 7

Preparation of Compound S7

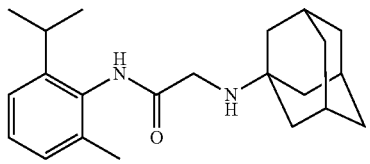

Compound S6 (2.4 g, 8.9 mmol) and 1-adamantylamine (2.0 g, 13 mmol) were dissolved in MeCN (30 mL), K$_2$CO$_3$ (1.9 g, 14 mmol) was added, and the solution was refluxed for 24 hours. After cooling to room temperature, the mixture was filtered over celite and concentrated. The residue was then dissolved in CH$_2$Cl$_2$ and filtered over a pad of silica gel (eluent 10% MeOH in CH$_2$Cl$_2$). Removal of the solvent in vacuo provided S7 (3.0 g, 94%) as a peach solid. $^1$H NMR δ 9.15 (br s, 1H), 7.18 (m, 1H), 7.16 (m, 1H), 7.09 (m, 1H), 3.44 (s, 2H), 3.04 (m, 1H), 2.23 (s, 3H), 2.11 (m, 3H), 1.58-1.72 (m, 14H), 1.20 (d, J=6.9 Hz, 6H). $^{13}$C NMR δ 171.9, 145.2, 135.6, 132.8, 128.1, 127.5, 123.3, 51.1, 44.0, 42.9, 36.5, 29.5, 28.7, 23.4, 18.8. HRMS (FAB+): Calculated—341.2593, Found—341.2603.

Example 8

Preparation of Compound S8

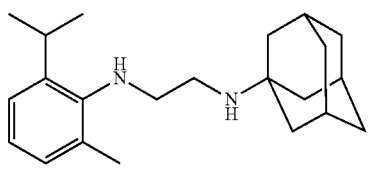

Lithium aluminum hydride (1.0 g, 26 mmol) was added portion-wise to a 0° C. solution of compound S7 (3.0 g, 8.8 mmol) in THF (45 mL), and the solution was brought to room temperature, then refluxed for 72 hours. The mixture was then cooled to 0° C., and water (1.0 mL), 10% aq. NaOH (1.0 mL), then additional water (1.0 mL) were added sequentially. The solution was dried with MgSO$_4$, filtered, and concentrated. Flash chromatography of the residue (SiO$_2$, using 66% Et$_2$O in pentanes) provided S8 (1.8 g, 62%) as a yellow oil. $^1$H NMR δ 7.08 (m, 1H), 6.98 (m, 1H), 6.91 (m, 1H), 3.30 (m, 1H), 3.06 (m, 2H), 2.86 (m, 2H), 2.32 (s, 3H), 2.08 (m, 3H), 1.59-1.73 (m, 15H), 1.23 (d, J=6.9 Hz, 6H). $^{13}$C NMR δ 145.1, 140.8, 130.6, 128.4, 123.6, 122.4, 51.1, 50.1, 42.9, 42.5, 40.7, 36.6, 29.5, 27.5, 24.0, 19.1. HRMS (FAB+): Calculated—327.2800, Found—327.2800.

Example 9

Preparation of Compound S9

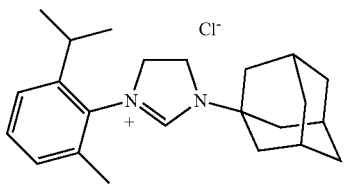

A solution of compound S8 (1.3 g, 4.0 mmol) in Et$_2$O (7.0 mL) was treated with HCl (4.0 mL, 2.0 M in Et$_2$O), and stirred for 15 minutes at room temperature. The solid was then filtered, washed with Et$_2$O, dried, suspended in CH(OEt)$_3$, and refluxed for 2 hours. The solution was cooled to room temperature and then concentrated. The resulting solid residue was washed rigorously with Et$_2$O to provide S9 (0.75 g, 50%) as a tan solid. $^1$H NMR δ 8.79 (br s, 1H), 7.32 (m, 1H), 7.22 (m, 1H), 7.13 (m, 1H), 4.55 (m, 1H), 4.43 (m, 2H), 4.25 (m, 1H), 2.93 (m, 1H), 2.41 (s, 3H), 2.27 (m, 3H), 2.18-2.08 (m, 6H), 1.74 (m, 6H), 1.28 (d, J=6.8 Hz, 6H). $^{13}$C NMR δ 156.0, 146.5, 135.9, 132.0, 130.6, 129.2, 124.8, 58.2, 52.1, 45.5, 41.1, 35.4, 29.2, 28.7, 24.8, 24.2, 18.7. HRMS (FAB+): Calculated—337.2644, Found—337.2652.

Example 10

Preparation of Catalyst S10

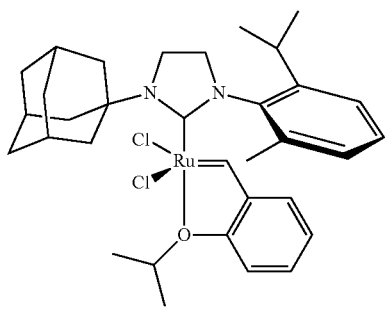

S10

In a glovebox, KCOMe$_2$Et (75 mg, 0.57 mmol) was added to a suspension of compound S9 (0.19 g, 0.52 mmol) in hexanes (6.0 mL). The solution was stirred at 35° C. for 30 minutes, and then S4 (0.31 g, 0.52 mmol) was added, at which point the solution was removed from the glovebox. The solution was stirred for 2 hours at 65° C. and then cooled to room temperature. The resulting precipitate was filtered and washed thoroughly with warm hexanes to provide S10 (0.22 g, 65%) as a green solid. $^1$H NMR δ 16.9 (s, 1H), 7.54 (m, 1H), 7.49 (m, 1H), 7.22 (m, 1H), 6.92 (m, 1H), 6.87 (m, 1H), 6.85 (m, 1H), 5.07 (m, 1H), 3.98-4.11 (m, 2H), 3.84-3.92 (m, 2H), 3.15 (m, 1H), 2.96 (m, 5H), 2.42 (m, 2H), 2.32 (s, 3H), 1.94 (m, 3H), 1.83 (m, 3H), 1.69 (d, J=6.2 Hz, 3H), 1.60 (d, J=6.2 Hz, 3H), 1.18 (d, J=6.8 Hz, 3H), 0.89 (d, J=6.8 Hz, 3H). $^{13}$C NMR δ 310.5, 208.2, 152.5, 148.7, 145.2, 140.6, 137.9, 130.6, 129.1, 128.9, 124.8, 123.8, 122.5, 113.2, 74.2, 57.2, 52.7, 44.5, 42.2, 36.1, 30.0, 27.6, 25.5, 23.8, 22.7, 22.3, 18.9. HRMS (FAB+): Calculated—656.1875, Found—656.1894.

Example 11

Preparation of Catalyst 8

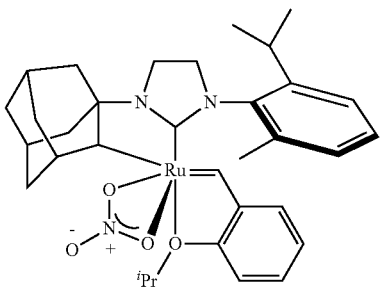

8

In a glovebox, a solution of NaOPiv (0.30 g, 1.5 mmol) in MeOH (2.0 mL) was added to a solution of S10 (0.15 g, 0.15 mmol) in THF (2.0 mL). The mixture was removed from the glovebox, heated at 50° C. for 21 hours, and then brought back into the glovebox and concentrated. The residue was taken in CH$_2$Cl$_2$, filtered over a pad of celite, dissolved in THF (8.0 mL), and then ammonium nitrate (0.12 g, 1.5 mmol) was added. Following stirring for 3 hours, the mixture was concentrated. The residue was then taken in CH$_2$Cl$_2$, filtered over a pad of celite, and concentrated. Rigorous washing of the resulting solid with Et$_2$O provided 8 (0.70 g, 72%) as a purple solid. $^1$H NMR δ 15.0 (s, 1H), 7.48 (m, 1H), 7.42 (m, 1H), 7.13 (m, 1H), 7.08 (m, 1H), 6.99 (m, 1H), 6.97 (m, 1H), 5.10 (m, 1H), 3.95 (m, 1H), 3.78-3.99 (m, 4H), 3.72 (m, 1H), 3.15 (m, 1H), 2.23 (m, 1H), 2.18 (s, 3H), 2.18 (overlapped, 1H), 2.06 (m, 1H), 1.99 (m, 1H), 1.92 (m, 1H), 1.72 (m, 1H), 1.65 (m, 1H), 1.59 (m, 1H), 1.55 (m, 2H), 1.48 (d, J=6.2 Hz, 3H), 1.23 (d, J=6.8 Hz, 3H), 1.17 (d, J=6.2 Hz, 3H), 1.12 (d, J=6.8 Hz, 3H), 0.98 (m, 2H), 0.24 (m, 1H). $^{13}$C NMR δ 266.4, 213.1, 154.7, 147.6, 143.1, 138.0, 137.3, 128.7, 128.3, 127.1, 124.0, 123.4, 123.4, 112.9, 74.4, 67.6, 52.6, 43.2, 42.3, 40.3, 37.9, 37.7, 37.6, 33.3, 31.0, 29.8, 28.3, 26.3, 23.6, 21.4, 20.6, 17.5. HRMS (FAB+): Calculated—646.2219, Found—646.2239.

Example 12

Preparation of Catalyst 9

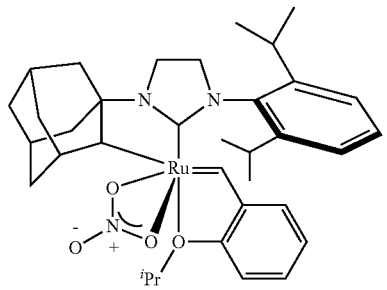

9

In a glovebox, a 250 mL Schlenk flask was charged with 4 (0.50 g, 0.73 mmol), NaOPiv (0.92 g, 7.4 mmol), THF (32 mL), and MeOH (16 mL). The flask was sealed, removed from the box, and heated to 40° C. for 4 days at which point the solution was a deep purple color. The solvent was removed under high vacuum and the Schlenk flask transferred back into the glovebox where the reside was dissolved in CH$_2$Cl$_2$ (80 mL), filtered through celite, and concentrated to a deep purple residue consisting of a mixture of the C—H activated product and pivalic acid. To this residue was added ammonium nitrate (0.72 g, 9.0 mmol) and THF (35 mL). The reaction was allowed to stir for 3 h inside the glovebox, after which the solvent was removed under vacuum. The residue was dissolved in C$_6$H$_6$ (70 mL), filtered through celite, and concentrated. The resulting residue was triturated with Et$_2$O (3×15 mL) to give 9 as a bright purple powder (100 mg, 20%). $^1$H NMR (500 MHz, C$_6$D$_6$) δ 15.21 (s, 1H), 7.45 (dd, J=7.4, 1.7 Hz, 1H), 7.19 (qd, J=5.8, 5.2, 2.5 Hz, 3H), 7.00 (dd, J=6.8, 2.5 Hz, 1H), 6.85 (t, J=7.4 Hz, 1H), 6.47 (d, J=8.4 Hz, 1H), 4.54 (hept, J=6.3 Hz, 1H), 4.10 (s, 1H), 3.83-3.71 (m, 2H), 3.59 (ddd, J=11.7, 10.1, 8.1 Hz, 1H), 3.36 (ddd, J=11.0, 9.7, 8.1 Hz, 1H), 3.26-3.15 (m, 2H), 2.25 (t, J=3.0 Hz, 1H), 2.06 (p, J=3.3 Hz, 1H), 1.94 (tt, J=11.9, 2.4 Hz, 2H), 1.77 (overlapped, 2H), 1.75 (d, J=6.7 Hz, 3H), 1.63 (p, J=3.4 Hz, 1H), 1.55-1.44 (m, 2H), 1.43 (overlapped, 1H), 1.42 (d, J=6.4 Hz, 3H), 1.20 (d, J=6.9 Hz, 3H), 1.16 (d, J=6.8 Hz, 3H), 1.14 (overlapped, 1H), 1.13 (d, J=6.8 Hz, 3H), 1.10 (overlapped, 1H), 0.97 (d, J=6.1 Hz, 3H), 0.58 (dt, J=12.2, 2.6 Hz, 1H). $^{13}$C NMR (126 MHz, C$_6$D$_6$) δ 267.5, 211.9, 154.8, 147.5, 147.4, 143.4, 135.6, 129.2, 126.9, 124.8, 124.2, 123.4, 123.4, 113.2, 74.4, 66.4, 63.2, 54.1, 43.0, 41.6, 40.3, 38.0, 37.8, 37.7, 33.3, 30.9, 29.8, 29.0, 28.7, 27.9, 26.8, 23.6, 23.1, 21.1, 20.3. HRMS (FAB+): Calculated—674.2566, Found—674.2532.

General Procedure for Homodimerization Reactions

In a glovebox, a 4 ml vial was charged with catalyst (0.014 mmol) and THF (1.0 mL) to make a stock solution (0.014 M). A portion of the catalyst stock solution (70 µL, ca. 1.0 µmol) was added to a 4 mL vial containing substrate (1.0 mmol) and THF (100 µL, ca. 3.3 M). The vial was then placed into an aluminum block on an IKA temperature-controlled hotplate preheated to 35° C., and the reaction was stirred while open to the glovebox atmosphere. After completion of the reaction (as determined by $^1$H NMR spectroscopy), the vial was removed from the glovebox, quenched with oxygen, and the product was isolated either via flash chromatography on silica gel or by removal of starting material in vacuo according to literature procedures (see Keitz, B. K.; Endo, K.; Herbert, M. B.; Grubbs, R. H. *J. Am. Chem. Soc.* 2011, 133, 9686). The percentage of Z-olefin product was determined by $^1$H NMR spectroscopy. All spectra were consistent with previous literature reports (see Keitz, B. K.; Endo, K.; Herbert, M. B.; Grubbs, R. H. *J. Am. Chem. Soc.* 2011, 133, 9686).

Example 13

General Procedure for the Synthesis of Compound 17 Using Catalyst 9

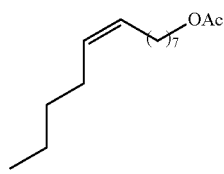

17

In a glovebox, a 20 mL vial was charged with 16 (520 µL, 2.5 mmol), 15 (3.1 mL, 25 mmol), and THF (1.4 mL). 9 (8.5 mg, 0.013 mmol, 0.5 mol %) was added and the reaction was stirred at 35° C. in an open vial for 2 hours. The vial was removed from the glovebox, quenched with ethyl vinyl ether (1.5 mL) and stirred for 1 hour. The solvent was then removed in vacuo. The crude mixture was purified by flash column chromatography (SiO$_2$, hexane to 4% ethyl acetate in hexanes) two times to provide the pure Z-isomer of 17 (430 mg, 71%). $^1$H NMR (500 MHz, CDCl$_3$) δ 5.34 (m, 2H), 4.05 (t, J=6.8 Hz, 2H), 2.00-2.04 (m, 7H), 1.60-1.63 (m, 2H), 1.29-1.36 (m, 12H), 0.88-0.91 (m, 3H). $^{13}$C NMR (126 MHz, CDCl$_3$) δ 171.4, 130.1, 129.9, 64.8, 32.1, 29.8, 29.3, 28.7, 27.3, 27.1, 26.0, 22.5, 21.2, 14.1. HRMS (EI+): Calculated—241.2168, Found—241.2174.

Example 14

Synthesis of Compound 17 at 1 mol % Catalyst Loading

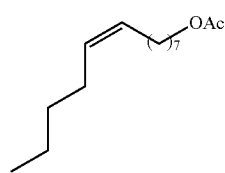

17

Following the general procedure, 9 (1.7 mg, 0.0025 mmol, 0.1 mol %) was added to a solution of 16 (520 µL, 2.5 mmol), 15 (3.1 mL, 25 mmol) in THF (1.4 mL) to produce 17 (360 mg, 60%).

General Procedure for Macrocyclizations Using Catalyst 9

In a glovebox, a 500 mL Strauss flask was charged with a solution of diene (1 equiv, ca. 0.45 mmol) in dichloroethane (5.0 mM, 90 mL), and a solution of 9 (7.5 mol %) dissolved in dichloroethane (1.0 mL) was added. The flask was sealed, brought out of the glovebox, and subjected to a single freeze/pump/thaw cycle. The flask was kept under a static vacuum of ca. 20 mtorr and heated at 60° C. After 24 hours, the mixture was cooled, quenched with excess ethyl vinyl ether, and concentrated. Flash chromatography of the residue (SiO$_2$, using 2% Et$_2$O in pentanes for compounds 18 and 19, and 10% Et$_2$O in pentanes for compound 20) provided the product. E/Z ratios were determined by quantitative $^{13}$C NMR. Quantitative $^{13}$C measurements were acquired at 126 MHz (decoupled, without NOE, 13 second delay time). E/Z macrocycles can be readily differentiated through careful analysis of their 1H, 13C, and HSQC spectra, as the carbon atoms a to the olefin moiety in the E-isomers are located significantly more downfield then the corresponding carbon atoms in the Z-isomers, see: Breitmaier, E.; Voelter, W. *Carbon-13 NMR Spectroscopy: High Resolution Methods and Applications in Organic Chemistry and Biochemistry.* Verlag Chemie: Weinheim, 1987.

Dienes 18a-20a were synthesized as disclosed previously: Marx, V. M.; Herbert, M. B.; Keitz, B. K.; Grubbs, R. H. *J. Am. Chem. Soc.* 2013, 135, 94.

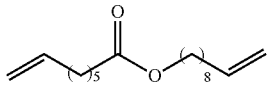

18a

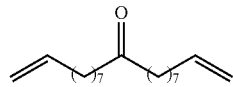

19a

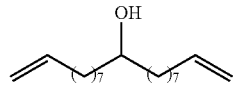

20a

Example 15

Preparation of Compound 18

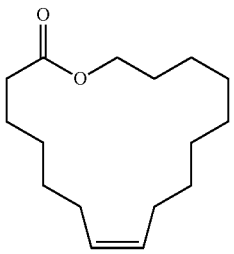

According to the general procedure for macrocyclizations, diene 18a (62 mg, 0.22 mmol) was reacted with 9 (12 mg, 0.018 mmol) to provide 18 (35 mg, 64% yield, >95% Z as determined by $^1$H- and $^{13}$C-NMR) as a colorless oil. $^1$H NMR δ 5.32 (m, 2H), 4.13 (t, J=5.4 Hz, 2H), 2.33 (t, J=6.5 Hz, 2H), 2.04 (m, 4H), 1.63 (m, 4H), 1.21-1.43 (m, 14H). $^{13}$C NMR δ 174.0, 130.2, 130.0, 63.7, 34.6, 29.4, 28.8, 28.7, 28.5 (2C), 28.4, 27.7, 27.0, 26.8, 25.3 (2C). HRMS (EI+): Calculated—252.2089, Found—252.2084.

Example 16

Preparation of Compound 19

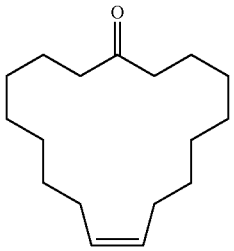

According to the general procedure for macrocyclizations, diene 19a (60 mg, 0.22 mmol) was reacted with 9 (12 mg, 0.018 mmol) to provide 19 (20 mg, 36% yield, >95% Z as determined by $^1$H- and $^{13}$C-NMR) as a colorless solid. $^1$H NMR δ 5.34 (m, 2H), 2.40 (t, J=6.7 Hz, 4H), 2.01 (m, 4H), 1.62 (m, 4H), 1.21-1.39 (m, 16H). $^{13}$C NMR δ 212.6, 130.2 (2C), 42.5 (2C), 29.0 (2C), 28.6 (2C), 28.2 (2C), 28.1 (2C), 26.7 (2C), 23.9 (2C). HRMS (EI+): Calculated—250.2297, Found—250.2289.

Example 17

Preparation of Compound 20

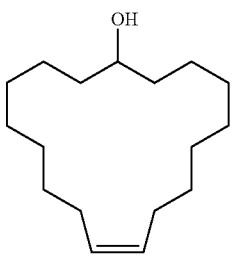

According to the general procedure for macrocyclizations, diene 20a (62 mg, 0.22 mmol) was reacted with 9 (12 mg, 0.018 mmol) to provide 20 (23 mg, 42% yield, >95% Z as determined by $^1$H- and $^{13}$C-NMR) as a colorless solid. $^1$H NMR δ 5.34 (m, 2H), 3.72 (m, 1H), 2.04 (m, 4H), 1.50 (m, 4H), 1.22-1.40 (m, 21H). $^{13}$C NMR δ 130.2 (2C), 70.4, 35.7 (2C), 29.0 (2C), 28.2 (2C), 28.0 (2C), 27.9 (2C), 26.8 (2C), 23.5 (2C). HRMS (EI+): Calculated—252.2453, Found—252.2463.

Example 18

Preparation of Catalyst 6

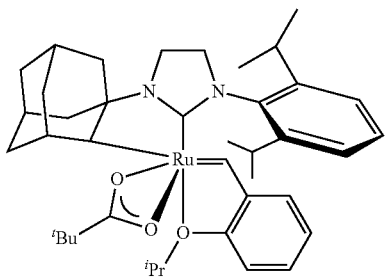

In a glovebox, a 25 mL Schlenk flask was charged with 4 (50 mg, 73 μmol), NaOPiv (92 mg, 0.74 mmol), THF (6 mL), and MeOH (3 mL). The flask was sealed, removed from the box, and heated to 40° C. for 4 days at which point the solution was a deep purple color. The solvent was removed under high vacuum and the Schlenk flask transferred back into the glovebox where the residue was dissolved in $CH_2Cl_2$ (20 mL), filtered through celite, and concentrated to a deep purple residue consisting of a mixture of the C—H activated product and pivalic acid. The crude mixture was purified by pipette column ($SiO_2$, eluent 20% $Et_2O$ in pentane) three times and subsequently recrystallized from pentane to provide 6 as a bright purple solid (7 mg, 13%). NMR data was consistent with the structure of 6.

Example 19

Results of Cross Metathesis Studies: Allyl benzene (Table 4)

Scheme 4. Homodimerization of allyl benzene.

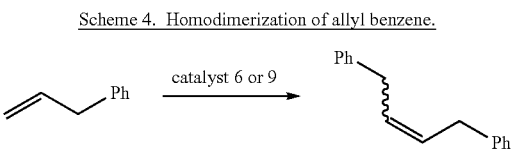

TABLE 4

| entry | catalyst | loading (mol %) | substrate conc. (M) | temp. (° C.) | time (h) | conversion (%)[a] | Z (%)[a] |
|---|---|---|---|---|---|---|---|
| 1 | 6 | 0.1 | 3.3 | 35 | 1 | 93 | 95 |
| 2 | 6 | 0.01 | 3.3 | 35 | 3 | 33 | 91 |
| 3 | 9 | 0.1 | 3.3 | 35 | 2 | 96 | 98 |
| 4 | 9 | 0.1 | 1 | r.t | 6.5 | 94 | 98 |
| 5 | 9 | 0.01 | 3.3 | 35 | 2.5 | 14 | >99 |

[a]Determined by $^1$H NMR.

Catalyst 6: 95% Z-selectivity and 93% conversion after 1 hr. were obtained from allyl benzene under the conditions of 0.1 mol % catalyst 6 in 3.3M THF at 35° C. (entry 1). After 1 hr., a significant amount of Z-degradation is observed over time (62% Z after one day). When the amount of catalyst was reduced (entry 2; 0.01 mol %), Z-selectivity remained high, while conversion reached 33% after 3 hours and did not increase significantly thereafter. However, 33% conversion at 0.01 mol % catalyst loading corresponds to a TON of 3300, representing a marked improvement over previous ruthenium metathesis catalysts.

Catalyst 9: Using the 0.1 mol % of the nitrato-containing catalyst, 98% Z-selectivity and 96% conversion were achieved after 2 hrs. at 35° C. (entry 3). Z-degradation does occur over time, but at a lower rate (77% cis-olefin after one day). Next, the homodimerization was run at room temperature in tandem with a decrease in substrate concentration to 1M, giving 98% Z and 94% conversion after 6.5 hrs (entry 4). Finally, the amount of catalyst was again reduced to 0.01%, providing the homodimer in 14% conversion (TON 1400) and >99% Z-selectivity after 2.5 hrs. at 35° C. (entry 5).

Example 20

Results of Cross Metathesis Studies: 4-penten-1-ol (Table 5)

Scheme 5. Homodimerization of 4-penten-1-ol..

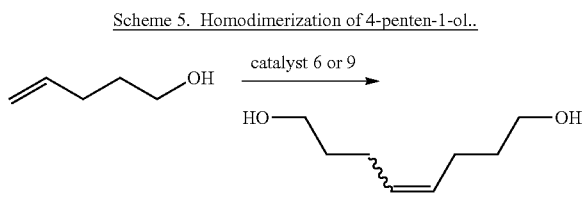

TABLE 5

| entry | catalyst | loading (mol %) | substrate conc. (M) | temp. (° C.) | time (h) | conversion (%)[a] | Z (%)[a] |
|---|---|---|---|---|---|---|---|
| 1 | 6 | 0.1 | 3.3 | 35 | 2.5 | 83 | 94 |
|   |   |   |   |   | 6 | 88 | 88 |
| 2 | 9 | 0.1 | 3.3 | 35 | 2 | 77 | 98 |
|   |   |   |   |   | 3 | 81 | 95 |
| 3 | 9 | 0.1 | 1 | r.t | 6.5 | 25 | 99 |
| 4 | 9 | 0.01 | 3.3 | 35 | 2.5 | 17 | 98 |

[a]Determined by $^1$H NMR.

Catalyst 6: The homodimerization of 4-penten-1-ol was also tested at 35° C. and 0.1 mol % loading. The homocross product was obtained in reasonable conversion (83%) and high selectivity (94%) (entry 1). Some Z-degradation is observed over time; accordingly, the reaction is stopped after 2.5 hours.

Catalyst 9: Similar results were obtained using catalyst 9 under the same conditions (95% Z-selectivity and 81% conversion after 3 hours); again, some Z-degradation is observed over time (entry 2). When the reaction is run at room temperature, a conversion of 25% is achieved after 6.5 hrs. (TON 2500), along with a Z-selectivity of 99% (entry 3). Finally, lowering the amount of catalyst to 0.01 mol % gave 17% conversion (TON 1700) with 98% Z-selectivity after 2.5 hours at 35° C. (entry 4).

Example 21

Results of Cross Metathesis Studies: 10-methyl undecenoate (Table 6)

Scheme 6. Homodimerization of 10-methyl undecanoate.

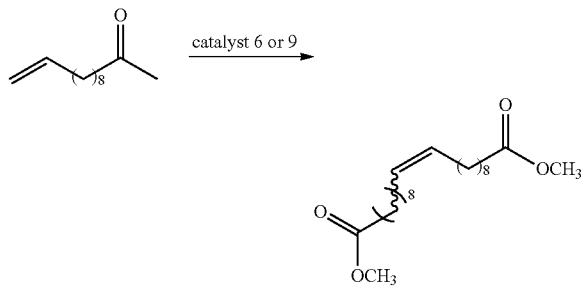

TABLE 6

| entry | catalyst | loading (mol %) | substrate conc. (M) | temp. (° C.) | time (h) | conversion (%)[a] | Z (%)[a] |
|---|---|---|---|---|---|---|---|
| 1 | 6 | 0.1 | 3.3 | 35 | 6 | 71 | 88 |
| 2 | 9 | 0.1 | 3.3 | 35 | 2 | 93 | 99 |
| 3 | 9 | 0.1 | 1 | r.t | 6.5 | 88 | 98 |
| 4 | 9 | 0.01 | 3.3 | 35 | 7.5 | 81 | 98 |

[a]Determined by $^1$H NMR.

Catalyst 6: At the standard conditions of 0.1 mol % catalyst loading and 35° C., catalyst 6 afforded the 10-methyl undecenoate homodimer in 71% conversion and reasonable Z-selectivity (88%) after 6 hours (entry 1).

Catalyst 9: Under the same conditions, both conversion and Z-selectivity are significantly improved when using the nitrato-containing catalyst (93% conversion and 99% Z after 2 hours.) (entry 2). Keeping the amount of catalyst consistent but running the reaction at room temperature and a lower substrate concentration (1M) provided similarly high Z (98%) and 88% conversion (entry 3). When the amount of catalyst was reduced (entry 4, 0.01 mol %) both a high conversion and high Z-selectivity were achieved (81%, corresponding to a TON of 8100 and 98%, respectively).

Example 22

Results of ROMP Studies: Norbornene

Scheme 7. ROMP of norbornene.

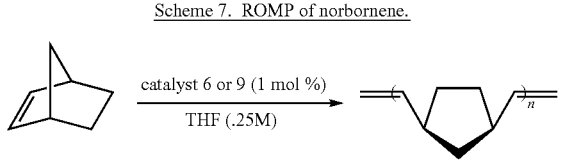

Ring opening metathesis polymerization of norbornene was performed with both catalysts. At 1 mol % catalyst loading and 0.25M substrate concentration in THF, catalyst 6 afforded polynorbornene in 27% yield and with 58% Z-selectivity, while under the same conditions catalyst 9 gave significantly better results (76% yield and 79% Z-selectivity).

It is to be understood that while the invention has been described in conjunction with specific embodiments thereof, that the description above as well as the examples that follow are intended to illustrate and not limit the scope of the invention. Other aspects, advantages, and modifications within the scope of the invention will be apparent to those skilled in the art to which the invention pertains.

What is claimed is:

1. A process for preparing a macrocyclic compound comprising reacting a C—H activated metathesis catalyst represented by formula 9 with a diene, wherein the diene is represented by the formula 18a

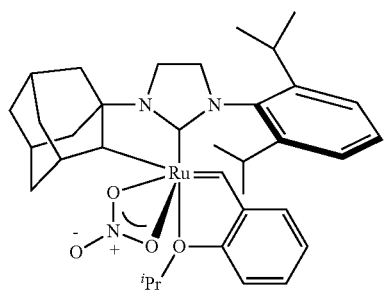

9

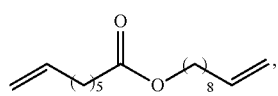

18a and the macrocyclic compound is represented by the formula 18

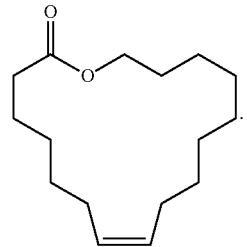

18

2. A process for preparing a macrocyclic compound comprising reacting a C—H activated metathesis catalyst represented by formula 9 with a diene, wherein the diene is represented by the formula 19a

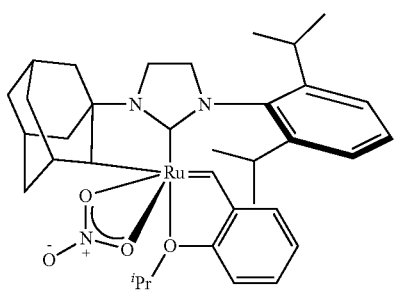

9

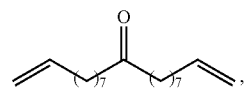

19a and the macrocyclic compound is represented by the formula 19

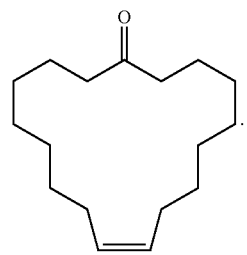

19

3. A process for preparing a macrocyclic compound comprising reacting a C—H activated metathesis catalyst represented by formula 9 with a diene, wherein the diene is represented by the formula 20a

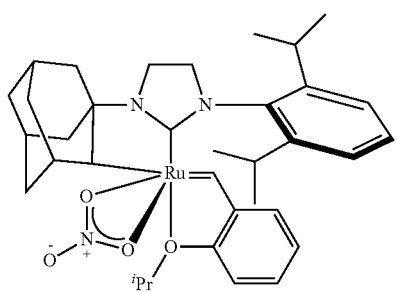
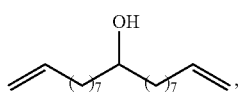
and the macrocyclic compound is represented by the formula 20
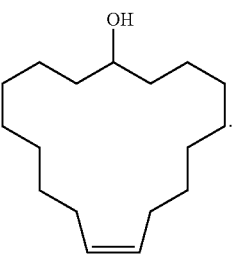
* * * * *